United States Patent [19]

Simmons, et al.

[11] Patent Number: 4,783,866
[45] Date of Patent: Nov. 15, 1988

[54] THERAPY PILLOW WITH REMOVABLE THERAPEUTIC GEL PACK

[76] Inventor: Ethel D. Simmons, 811 S. Bedford St., #301, Los Angeles, Calif. 90035; Lee Kudrow, 16542 Ventura Blvd., Encino, Calif. 91436

[21] Appl. No.: 2,052

[22] Filed: Jan. 12, 1987

[51] Int. Cl.⁴ ............................ A47G 9/00; A61F 7/00
[52] U.S. Cl. ........................................ 5/441; 5/442; 5/421; 128/403
[58] Field of Search .................... 5/421, 434, 436, 441, 5/438, 442; 128/403, 402, 380, 376, 377; 297/393; 62/261

[56] References Cited

U.S. PATENT DOCUMENTS

| | | | |
|---|---|---|---|
| D. 33,613 | 11/1900 | Hogan et al. | D6/604 |
| D. 33,763 | 12/1900 | Meinecke et al. | D6/604 |
| D. 59,900 | 12/1921 | Marsh | D6/604 |
| D. 124,296 | 12/1940 | Thompson | D6/601 |
| D. 177,472 | 4/1956 | Huntington | D6/601 |
| D. 255,966 | 7/1980 | Stadel | 5/441 |
| D. 277,059 | 1/1985 | Boone | 5/435 |
| 750,104 | 1/1904 | Eggers . | |
| 1,343,357 | 6/1920 | Eggers . | |
| 2,803,115 | 8/1957 | Shepherd . | |
| 3,312,987 | 4/1967 | Emery | 5/441 |
| 3,463,161 | 8/1969 | Andrassy . | |
| 3,545,230 | 12/1970 | Morse . | |
| 3,780,537 | 12/1973 | Spencer | 128/403 |
| 3,822,705 | 7/1974 | Pilotte | 128/403 |
| 3,840,918 | 10/1974 | Shavie | 5/436 |
| 3,871,376 | 3/1975 | Kozak | 128/403 |
| 3,885,403 | 5/1975 | Spencer | 128/403 |
| 3,900,035 | 8/1975 | Welch et al. | 128/402 |
| 4,055,188 | 10/1977 | Pelton | 128/403 |
| 4,092,982 | 6/1978 | Salem | 128/402 |
| 4,161,794 | 7/1979 | Darnfors | 5/441 |
| 4,204,543 | 5/1980 | Henderson | 128/403 |
| 4,325,151 | 4/1982 | Wu | 5/441 |
| 4,345,347 | 8/1982 | Kantor | 5/441 |
| 4,468,823 | 9/1984 | Tounjian | 5/417 |
| 4,676,247 | 6/1987 | Van Cleve | 128/403 |

FOREIGN PATENT DOCUMENTS

| | | | |
|---|---|---|---|
| 838455 | 6/1960 | United Kingdom | 297/293 |
| 1048632 | 4/1966 | United Kingdom | 5/436 |

Primary Examiner—Alexander Grosz
Attorney, Agent, or Firm—David O'Reilly

[57] ABSTRACT

A therapy pillow having a cold pack specially constructed and contoured to provide intimate contact with the occipital region of the head. The pillow constructed and contoured to fit partially around the neck and tapered so that the surface portion of the pillow will apply an even force to the occipital region of the head. A pocket provided in the pillow receives a specially contoured container filled with a temperature retaining material providing a cold pack which will relieve migraine or muscular contraction headaches when applied to the head. The specially constructed pocket is lined with a moisture resistant material and is easily and quickly opened and closed for receiving the cold pack.

5 Claims, 1 Drawing Sheet

U.S. Patent    Nov. 15, 1988    4,783,866
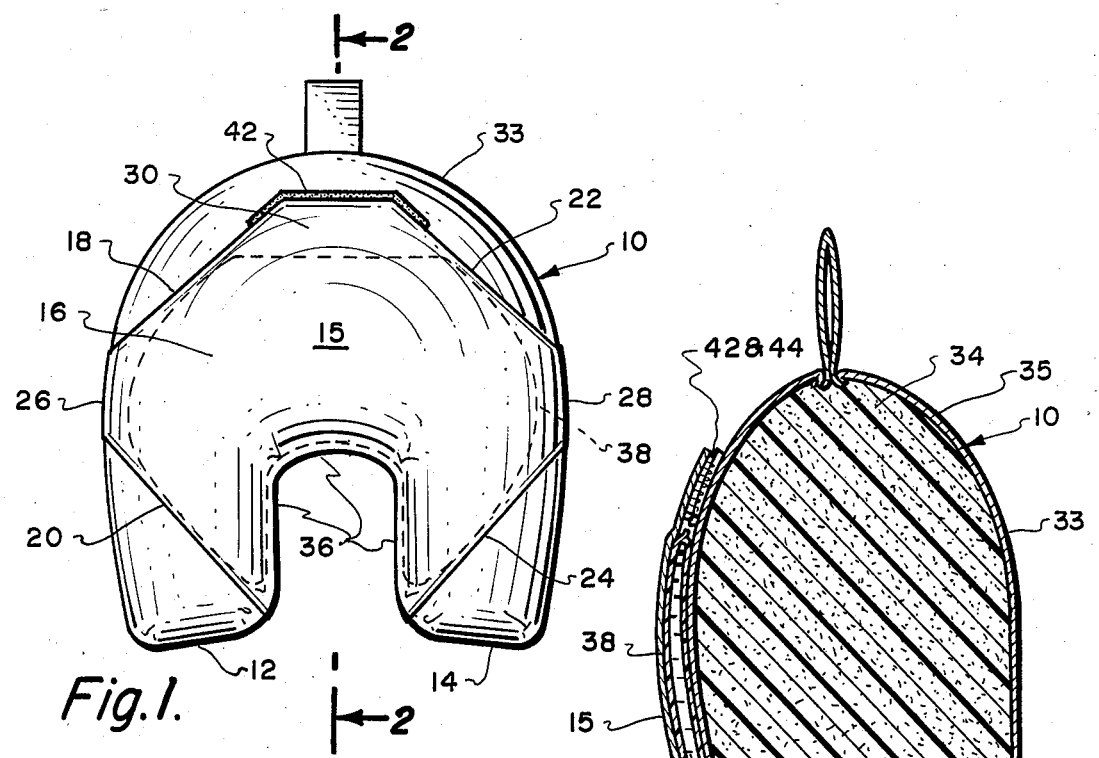
Fig.1.
Fig. 2.
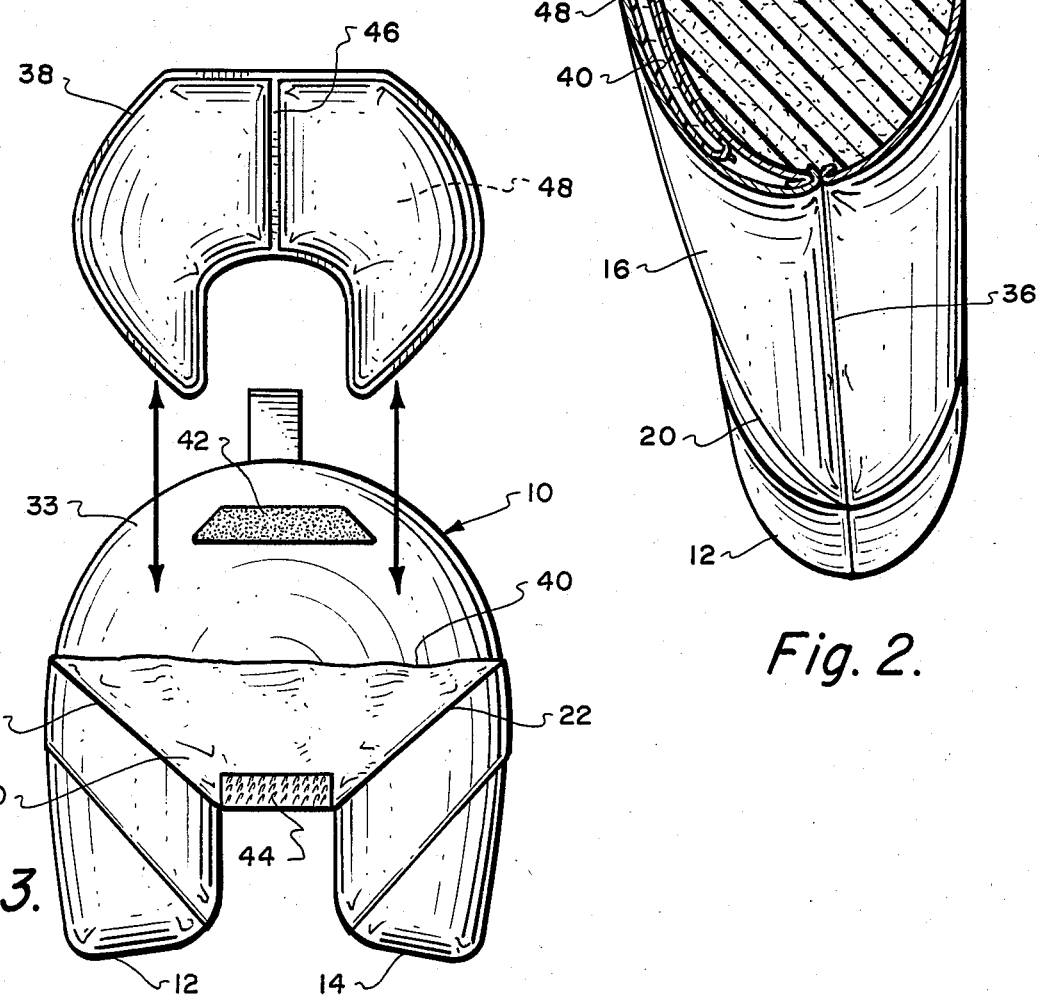
Fig.3.

THERAPY PILLOW WITH REMOVABLE THERAPEUTIC GEL PACK

FIELD OF THE INVENTION

This invention relates to therapeutic devices for treatment of headaches, and more particularly relates to a therapy pillow having a removable cold pack.

BACKGROUND OF THE INVENTION

There are many devices available for treating strains and injuries by application of ice packs or hot water bottles. These devices combine hot or cold treatment with an elastic bandage so that the therapeutic effect of the hot or cold treatment can be applied in a manner that allows the patient to move about freely. In most cases these devices include flexible enclosures inserted in a bandage similar to the elastic bandage known as an "Ace" bandage, which can be wrapped around extremities such as the wrist, arm, hand, etc. The flexible enclosure usually has some liquid anti-freeze solution for absorbing a considerable amount of heat or cold, which will be retained for a period of time. The anti-freeze solution in the packets in these devices will provide an unfrozen slush at a low temperatures. After cooling or heating the device is then wrapped around the extremity, such as elbow, ankle, knee, etc. to treat the injured area.

One such device is disclosed and described in U.S. Pat. No. 3,900,035, issued Aug. 19, 1975, to Welch et al. This device has a shape of an elastic rectangular bandage having a plurality of bags filled with solution sewn into the elastic bandage. The bandage may then be wrapped around the extremity to apply the hot or cold therapeutic treatment.

Another patent which teaches a similar treating device is disclosed in U.S. Pat. No. 3,463,161, issued Aug. 26, 1969. This device discloses unique compositions which remain permanently plastic at low or high temperatures. The compositions disclosed will maintain desired temperatures for a long time and provide flexible soft, plastic products to be applied to various parts of the body. The Patent discloses devices which are shaped to apply to the particular portion of the body. The material is enclosed in a soft plastic container generally divided into compartments by barriers, quilting or use of dividers. One such device is disclosed as a "Icecap" which can be used to cover the scalp.

Various types of devices including compositions which retain temperature are known, and have been previously proposed by the devices disclosed in U.S. Pat. Nos. 750,104; 3,780,537; 3,822,705; 3,885,403; 3,871,376; 4,055,188; 4,092,982; and 4,204,543; which all describe devices for applying hot or cold treatment to various areas of the body of humans and animals. In some cases these Patents describe particular materials which maintain a gel-like consistency over a wide temperature range. One such material is commonly known by the trademark name of "Blue-Ice."

Materials for use in these hot and cold treatment devices are disclosed in U.S. Pat. Nos. 2,803,115; and 3,545,230 incorporated herein by reference. These devices disclose either a slurry comprised of a mixture of starch, water and borax; or a insoluable hydrophilic gel which when frozen can be molded into various geometric shapes which can retain that particular configuration as long as the material remains stiff. The devices disclosed in the latter Patent are well suited for use in portable coolers, insulated picnic baskets, and the like. The materials disclosed and treatments described in these devices are widely known for being employed in the treatment of humans and animals. Ice for example, has been employed for many years and is well known for relieving the discomfort of pain and swelling from injuries to arms and legs suffered in accidents, such as in athletics or other endeavors.

Also known in the art are pillows for providing comfort when sleeping, sitting, or resting in a chair or bed. Devices having such shapes are disclosed in U.S. Pat. Nos. Des. 177,472; 1,343,357; Des. 255,966; 4,161,794; and 4,345,347. Each of these devices provide head and neck support cushions for use in high back chairs, passenger seats, beds or wherever a person may comfortably lay down and rest his head on these contoured pillows.

The disadvantages and difficulties of these devices is that none are particularly adaptable or suitable for the treatment and management of headaches. The pillows while providing the comfort for resting the head in a high back chair or bed are not suitable for combination with the therapeutic flexible cooling devices described in the referenced patents, while the latter are not generally suitable to apply the heat or cooling with maximum effectiveness to the ares needed. Headaches, such as migraine or muscle tension headaches in the back of the head occur mostly in the occipital region and it has been discovered that application of cooling temperatures with an appropriately designed pillow can result in a decrease of headache pain.

Therefore, it is one object of the present invention to provide a therapeutic pillow having an integrally formed removable hot or cold pack for treatment of headaches.

Still another object of the present invention is to provide a pillow designed to provide proper support of the head and neck when applying therapeutic heating or cooling temperatures to the posterior part of the skull.

Still another object of the present invention is to provide a contoured pillow having a pocket for insertion of a bag filled with a temperature retaining material for application of cooling temperatures to the posterior region of the skull to treat headaches.

Still another object of the present invention is to provide a properly contoured pillow having a specially designed pocket with a moisture proof lining for receiving a bag of temperature retaining material for application to the posterior region of the head.

BRIEF DESCRIPTION OF THE INVENTION

The purpose of this invention is to provide a specially contoured pillow having a pocket for receiving a bag contoured to apply cooling or heating temperatures to the posterior region of the skull known as the occipital region.

The purposes of the invention are accomplished by providing a pillow contoured to fit around the neck and having a portion shaped to evenly apply force to the posterior portion of the skull when a person's head is resting on the pillow. The pillow is filled with a suitable polyester material, a foam material or soft material and includes a pocket shaped to receive a U-shaped bag filled with a temperature retaining material, such as that known by the Trademark "Blue-Ice." A variety of materials are available which could be used but it is preferred and desirable that the material be sufficiently pliant when cold to conform to the shape of the posterior or occipital region of the head of a person lying on the special contoured pillow. The pillow has a U-shape with legs or arms extending outward to encompass the posterior portion of a neck, bringing the posterior occipital region of the head in close intimate contact with the surface area of the pillow. The interior portion of the pocket for receiving the bag of temperature retaining is lined with a moisture-proof material to prevent condensation from soaking through to the surface of the pillow. The pocket is closed by a suitable closure such as snaps, or a hook-and-loop material such as the one sold under the trademark of Velcro, sewn to the pillow and a pocket flap.

In use, one or more bags of the temperature retaining material can be kept in a refrigerator or freezer to keep them cool. The pocket of the pillow is opened and a cool bag of temperature retaining material is inserted in the pillow. A patient would then lay or otherwise rest his head on the pillow with the extensions partially extending around the posterior portion of the neck and the occipital region of the head in intimate contact with the area covered by the cold pack. Treatment for about twenty minutes is effective to relieve headache pain.

The effect of the cold pack in intimate contact with the occipital region of the head decreases the metabolism of the muscles thereby decreasing spasm. In addition it constricts the superficial, and some deep, blood vessels in the area that the pillow is in contact with. This occurs because of the action of the cold pack and the design and contour of the pillow. This pillow therefore, can be effectively used to treat migraine and muscle contraction headaches which are two different kinds of headaches sharing the same physiological, or pathophysiological changes.

With a migraine headache there is a dilation of arteries and muscle contraction, while in the muscle contraction headache there is only muscle contraction. In either case the properly applied cold temperatures in combination with the specially designed contour of the pillow give the proper contact which will stop or relieve a headache. The results of the application of this pillow to moderate headaches, both migraine and muscle contraction headaches, results in relief which is as good or better then analgesics. The muscle contraction headache, sometimes known as "acute" muscle contraction headaches can easily be avoided by application of cold temperatures with the pillow for a period of about twenty minutes. This is similar to the use of an anelgesic only it can be quicker or better.

The above and other features of this invention will be fully understood from the following detailed description and the accompanying drawings, in which:

BRIEF DESCRIPTION OF THE DRAWING

FIG. 1 is a top view of a specially contoured pillow according to the invention.

FIG. 2 is a sectional view taken at 2—2 of FIG. 1.

FIG. 3 is a view of the specially contoured pillow illustrating the insertion of a cold pack into the pocket.

DETAILED DESCRIPTION OF THE INVENTION

The invention shown in FIG. 1 is for the purpose of headache management and treatment not previously possible with the therapeutic packs and pillows available. The pillow shown generally at 10 has extensions 12 and 14 which fit around the posterior portion of the neck to bring the surface area 16 of the pillow into close intimate contact with the posterior or occipital region of the head. The area 16 of the pillow 10 is covered by a pocket formed by a piece of material 15 bounded at 18, 20, 22 and 24 stitched to the upper surface of the pillow at 20 and 24 and at the edges of the pillow 26 and 28. The portions 18 and 22 are left free and are secured at 30 by a suitable non-bulky clasp such as by using "Velcro."

The therapy pillow has a tab handle, a head portion 35 and a thinner neck portion formed by extensions 12 and 14. A patch of material 15 covering area 16 of the pillow provides a pocket for receiving a flexible plastic container 38 filled with a temperature retaining material 48 such as "Blue-Ice". The pillow is covered with a suitable soft durable material 33 and has a soft polyester fluffy filling 34, a down or a non-allergic foam material.

The piece of material covering the area 16 is shaped to provide intimate contact with the posterior occipital region of the head. Additionally, as shown in FIG. 2, the pillow is thicker at the upper end 35 and tapers away toward the extensions 12 and 14 (FIG. 1). The piece of material 15 covering area 16 is sewn into the seam at 36 forming the U-shape cutout illustrated in FIG. 1.

A flexible bag 38, as shown in FIG. 3, filled with a temperature retaining material such as "Blue-Ice" is shaped to closely fit the pocket 40 formed between material 15 sewn to area 16 of the pillow and the pillow 10 itself as shown in FIG. 2. A fastener in the form of a hook-and-loop or "Velcro" material shown at 42 and 44 serves to close the pocket after insertion of bag 38. To be certain of intimate contact with the occipital region of the head by the cold pack formed by bag 38 a seam 46 may be provided in the bag to divide the filling 48 into two chambers, providing an even distribution for application to the occipital region on either side of the head.

The pocket 40 formed by material is lined with a moisture resistance material such as Therafoam suede. This material is comprised of 50% cotton and 50% polyester.

In use, the bag 38 is placed in freezer or refrigerator to chill the temperature retaining material or gel 48 in the cold pack. Once chilled to a sufficient degree the pack is inserted into the pocket 40 formed by material 15 covering area 16 (FIG. 1) of the pillow and pushed down well into the pocket to cover a portion of extensions 12 and 14. The pocket is then closed by securing fasteners 42 and 44. The patient may then lay on the pillow with extensions 12 and 14 extending around the neck bringing the posterior or occipital region of the head into close intimate contact with the surface area 16 of the pillow. The cold pack formed by the container 38 will then apply cooling treatment to relieve migraine or muscular contraction headaches in this region. Usually application for about 20 minutes is enough to provide significant relief.

The pillow can be used lying down in a bed or sitting up in a high back chair. In any event the specially contoured structure assures that the soothing effect of the cold pack in container 38 is intimately and evenly applied to the occipital region of the head. The moisture-proof lining of the pocket area prevents moisture caused by condensation on the surface of the bag from seeping though to the patient.

Thus, there has been disclosed a novel and unique therapeutic pillow specially designed and contoured and constructed for receiving a cold pack particularly constructed to apply therapeutic temperatures to the occipital region of the head. When applied to the posterior region of the head the cold pack results in a significant reduction of pain from migraine or muscular contraction headaches.

This invention is not to be limited by the embodiment shown in the drawings and described in the description which is given by way of example and not of limitation, but only in accordance with the scope of the appended claims.

What is claimed is:

1. A therapy pillow for treating headaches comprising;
    a cushioned pillow filled with a soft resilient material have a pair of extensions forming a substantially U-shape;
    said pair of extensions constructed to fit around the back and a portion of the sides of a neck;
    a pocket formed on at least one side of said pillow covering a substantial portion of said pillow and extending to near the end and in-seams to cover a substantial portion of said extensions;
    said pocket constructed to provide intimate contact over nearly the entire occipital region of a human head resting on said cushioned pillow when said extensions are around the neck;
    a flexible plastic container shaped to fit said pocket, said container being filled with a solution formulated to retain hot or cold temperatures for a substantial period of time;
    said flexible container being comprised of two chambers, adapted to provide an even distribution of solution to the occipital region on both sides of a human head;
    said pocket having an opening accessible from one side for insertion of said flexible plastic container with the heated or chilled solution, said opening being covered by a flap on said pocket;
    closure means for closing and securing said pocket flap after insertion of said flexible plastic container;
    whereby said pillow can be used to effectively treat headaches by providing intimate cushioned contact over nearly the entire occipital region of a human head resting on said pillow.

2. The therapy pillow according to claim 1 in which said pocket is lined with a moisture resistant material.

3. The therapy pillow according to claim 2 in which said moisture resistant material is 50% cotton and 50% polyester.

4. The therapy pillow according to claim 1 in which said flexible plastic container has a central seam separating said container into two equal halves.

5. The therapy pillow according to claim 1 in which said pockets are formed on both sides of said pillow.

* * * * *